(12) United States Patent
Nam et al.

(10) Patent No.: US 11,060,021 B2
(45) Date of Patent: Jul. 13, 2021

(54) CORE-SHELL NANOCOMPOSITE FOR METAL-ENHANCED FLUORESCENCE

(71) Applicant: SNU R&DB FOUNDATION, Seoul (KR)

(72) Inventors: Jwa Min Nam, Seoul (KR); Jae Ho Hwang, Seongnam-si (KR); Min Ho Kim, Seoul (KR); Jung Hoon Lee, Seoul (KR)

(73) Assignee: SNU R&DB Foundation, Seoul (KR)

( * ) Notice: Subject to any disclaimer, the term of this patent is extended or adjusted under 35 U.S.C. 154(b) by 389 days.

(21) Appl. No.: 15/542,439

(22) PCT Filed: May 20, 2015

(86) PCT No.: PCT/KR2015/005067
§ 371 (c)(1),
(2) Date: Jul. 9, 2017

(87) PCT Pub. No.: WO2015/178688
PCT Pub. Date: Nov. 26, 2015

(65) Prior Publication Data
US 2018/0044584 A1    Feb. 15, 2018

(30) Foreign Application Priority Data
May 20, 2014   (KR) .................. 10-2014-0060090

(51) Int. Cl.
| | | |
|---|---|---|
| G01N 21/64 | (2006.01) | |
| C09K 11/02 | (2006.01) | |
| C09K 11/58 | (2006.01) | |
| C09K 11/06 | (2006.01) | |
| G01N 33/58 | (2006.01) | |

(52) U.S. Cl.
CPC ............ C09K 11/025 (2013.01); C09K 11/02 (2013.01); C09K 11/06 (2013.01); C09K 11/58 (2013.01); G01N 21/648 (2013.01); G01N 33/582 (2013.01)

(58) Field of Classification Search
CPC .............................. G01N 21/648; C09K 11/58
See application file for complete search history.

(56) References Cited

U.S. PATENT DOCUMENTS

| | | | |
|---|---|---|---|
| 2008/0066549 A1* | 3/2008 | Oldham | G01N 21/648 73/579 |
| 2009/0022766 A1 | 1/2009 | Geddes | |
| 2011/0124008 A1* | 5/2011 | Nam | G01N 33/54346 435/7.1 |
| 2013/0029360 A1 | 1/2013 | Suh et al. | |
| 2013/0330839 A1* | 12/2013 | Suh | G01N 21/658 436/501 |

FOREIGN PATENT DOCUMENTS

| | | |
|---|---|---|
| JP | 2004-256915 | 9/2004 |
| JP | 2006-330683 | 12/2006 |
| JP | 2010-197746 | 9/2010 |
| WO | 2007/046406 | 4/2007 |
| WO | WO 2008/073175 A2 | 6/2008 |

OTHER PUBLICATIONS

Hui, Li et al., "Metal-enhanced fluorescent detection for protein microarrays based on a silver plasmonic substrate," Analyst, 2014, v. 139, pp. 1653-1660.
Rizia Bardhan et al., "Fluorescence Enhancement by Au Nanostructures: Nanoshells and Nanorods," ACS NANO, 2009, vol. 3(3), pp. 744-752.
Dong-Kwon Lim et al., "DNA-embedded Au/Ag core-shell nanoparticles," Chem. Commun., 2008, 5312-5314.
Dong-Kwon Lim et al., "Nanogap-engineerable Raman-active nanodumbbells for single-molecule detection," Nature Materials, Jan. 2010, vol. 9, pp. 60-67.

* cited by examiner

*Primary Examiner* — Paul S Hyun
(74) *Attorney, Agent, or Firm* — Don D. Cha; HDC Intellectual Property Law, LLP

(57) ABSTRACT

The present invention relates to a core-shell nanocomposite including fluorescent bodies disposed to have a uniform distance in a perpendicular direction from a surface thereof, to a method of manufacturing same, and to a use for a probe for metal-enhanced fluorescence.

16 Claims, 10 Drawing Sheets

| Dimension(nm) | 50.32(4.26) x 12.81(0.94) |
| --- | --- |
| Aspect ratio | 3.95(0.42) |
| Transverse mode (nm) | 510 |
| Longitudinal mode (nm) | 765 |
| $e_{520nm}(M^{-1}cm^{-1})$ | $1.374 \times 10^9$ |

CORE-SHELL NANOCOMPOSITE FOR METAL-ENHANCED FLUORESCENCE

TECHNICAL FIELD

The present invention relates to a core-shell nanocomposite including a fluorophore disposed to have a constant distance in a vertical direction from a surface thereof, a method of manufacturing the same, and a use of the core-shell nanocomposite as a probe for metal-enhanced fluorescence.

BACKGROUND ART

Despite the use of fluorescence in highly sensitive techniques, there is still a tremendous drive to reduce the limits of detection at sites at which single molecules are detectable. The limits of detection are generally restricted by a quantum yield of a fluorophore, autofluorescence of a sample, and photostability of the fluorophore. Therefore, the use of metallic nanostructures has increased suddenly to satisfactorily modify optical properties of the fluorophore and relax photophysical constraints. The use of fluorophore-metal interactions was termed metal-enhanced fluorescence (MEF) by Dr. Chris D. Geddes. The use of MEF includes applications of a metallic surface for enhanced detectability and photostability of the fluorophore, improved detection of proteins and DNA/RNA, self-quenched fluorescence emission of a labeled protein, improved wavelength-ratiometric sensing and amplified essay detection, etc. Dr. Geddes' research team has also developed many nanostructured surfaces for metal-enhanced fluorescence, such as silver islands, silver colloids, silver nanotriangles, silver nanorods, and fractal-like silver-treated surfaces. Several modes for silver deposition on glass and plastics in an optical or electrochemical aspect, and even modes using electrodes, have been developed. For example, a surface and silver-treated surface of glass are labeled with a fluorophore-protein complex, and the two surfaces are irradiated with the same laser excitation source to observe fluorescence. As a result, the enhanced fluorescence may be observed in the silver-treated surface, compared to the surface of the glass. In this case, the enhanced fluorescence does not arise from photons reflected from a mirrored surface, such as an image taken through an emission filter but actually arises from plasmon-coupling and amplification. Fluorescence signals may be potentially amplified up to several million times, and such a potential for amplifying the fluorescence signals is suitably applicable to biological science and microscopy whose chief interests are photon flux and detectability.

A plasmonic nanostructure has received much attention due to designable and useful optical properties, which may be applied to nanoantennae, surface-enhanced Raman scattering (SERS), and metal-enhanced fluorescence (MEF). In particular, a plasmonic metal nanostructure may have an enhanced fluorescence signal when a fluorophore is properly disposed on a surface of the metal nanostructure, and thus has a potential as a fluorophore probe exhibiting higher signal intensity. Development of MEF nanoprobes may be effectively used immediately in a variety of research and application fields including biological research and medicine because most conventional detection platforms are based on fluorescence. However, there are several problems related to commercialization of these structures. A deeper and more accurate understanding of the MEF mechanism is required, and a better method of synthesizing an MEF nanostructure having higher structural reproducibility and synthesis yield should be designed. Literally, an MEF enhancement factor of up to approximately $10^3$ for measurement of single molecules has been reported. However, the results based on the measurement of single or several molecules are somewhat misleading for actual applications using bulk samples, and an ensemble-average MEF enhancement factor in a solution sample is just at an approximately 50-fold level. Since a fluorescence signal may be quenched or enhanced according to a distance between a fluorophore and a surface of a metal, it is important to obtain stable and quantitative signal intensity from MEF probes. Also, such MEF probes should be stable to be effectively used under various conditions including various excitation laser wavelengths, a wide range of ligands and various buffer conditions.

DISCLOSURE

Technical Problem

The present inventors have endeavored to design probes having a novel structure, which has an excellent metal-enhanced fluorescence effect and simultaneously provides stable signals, and found that a nanocomposite having a core-shell structure, which is prepared by binding a polynucleotide having a constant length, which has one end labeled with a fluorophore, to surfaces of nanorods of a first metal via the other end of the polynucleotide, and introducing a shell of a second metal onto the nanorods of the first metal by adjusting a thickness of the introduced shell of the second metal so that the fluorophore is exposed by being spaced apart a constant distance from the shell of the second metal, may provide a fluorescence signal whose intensity is remarkably enhanced due to metal-enhanced fluorescence, and the fixed composite may also provide signals having higher reproducibility due to a remarkable decrease in signal variation since a silica shell is introduced into the nanocomposite so that the exposed fluorophore is embedded in the silica shell, and may exhibit an additional increase in fluorescence intensity when the silica shell further includes a fluorophore. Therefore, the present invention has been based on these facts.

Technical Solution

One aspect of the present invention provides a core-shell nanocomposite including a fluorophore disposed to have a constant distance in a vertical direction from a surface thereof, which includes nanorods of a first metal having a certain aspect ratio; a polynucleotide having a constant length, bound onto the nanorods of the first metal via one end thereof and having a fluorophore bound to the other end thereof; and a shell of a second metal formed on the nanorods of the first metal to which the polynucleotide is bound by adjusting a thickness to be spaced apart a constant distance from the fluorophore.

Another aspect of the present invention provides a method of manufacturing a core-shell nanocomposite including a fluorophore disposed to have a constant distance from a surface thereof in a vertical direction, which includes a first step of preparing nanorods of a first metal; a second step of binding a polynucleotide having a constant length, which has the fluorophore bound to one end thereof, onto the nanorods of the first metal; and a third step of forming a shell of a second metal on the nanorods of the first metal to which the polynucleotide is bound by adjusting a thickness to be spaced apart a constant distance from the fluorophore.

Still another aspect of the present invention provides a probe for metal-enhanced fluorescence including the core-shell nanocomposite.

Advantageous Effects

According to the core-shell nanocomposite of the present invention which includes a fluorophore disposed to have a constant distance in a vertical direction from a surface thereof, a probe having a novel structure capable of exhibiting an excellent metal-enhanced fluorescence effect and also providing stable signals can be provided by selecting two metals having similar lattice parameters, which can utilize a polynucleotide so that a fluorophore can be disposed at a location spaced apart a constant distance from the surface to maximize metal-enhanced fluorescence, introduce a shell with a uniform thickness and control a thickness of the introduced shell at a sub-nanometer level. Further, because a silica shell can be introduced to stabilize fluorescence signals, the core-shell nanocomposite can be effectively used as a probe to remarkably improve detection sensitivity in analysis using fluorescence.

BEST MODE

To solve the above problems, according to an aspect of the present invention, there is provided a core-shell nanocomposite including a fluorophore disposed to have a constant distance in a vertical direction from a surface thereof, which includes nanoparticles of a first metal; a linker having a constant length, bound onto the nanoparticles of the first metal via one end thereof and having the fluorophore bound to the other end thereof; and a shell of a second metal formed on the nanoparticles of the first metal to which the linker is bound by adjusting a thickness to be spaced apart a constant distance from the fluorophore.

According to another aspect of the present invention, there is provided a method of manufacturing a core-shell nanocomposite including a fluorophore disposed to have a constant distance from a surface thereof in a vertical direction, which includes a first step of preparing nanoparticles of a first metal; a second step of binding a linker having a constant length, which has the fluorophore bound to one end thereof, onto the nanoparticles of the first metal; and a third step of forming a shell of a second metal on the nanoparticles of the first metal to which the linker is bound by adjusting a thickness to be spaced apart a constant distance from the fluorophore.

According to still another aspect of the present invention, there is provided a probe for metal-enhanced fluorescence including the core-shell nanocomposite according to an aspect of the present invention Hereinafter, the present invention will be described in detail.

A core-shell nanocomposite according to the present invention is characterized by including a fluorophore disposed to have a constant distance in a vertical direction from a surface of a metal, thereby exhibiting a remarkable metal-enhanced fluorescence effect. In this case, it is important to 1) properly select a material of a metal shell to be introduced and 2) introduce a metal shell by adjusting a thickness of the metal shell so as to maximize a metal-enhanced fluorescence effect. When the metal shell is formed too thickly so that the fluorophore comes in contact with a surface of the metal or is too close to the surface of the metal, excitation energy may be thrown away by being conducted rather than inducing fluorescence enhancement through resonance.

The term "metal-enhanced fluorescence (MEF)" refers to a phenomenon in which the intensity of fluorescence signals is enhanced by the interaction of a fluorophore and a metal disposed close to the fluorophore, compared to that enhanced by the fluorophore itself. Specifically, a metal-enhanced fluorescence phenomenon may occur as a result of the interaction between the fluorophore in an excited state and an induced surface plasmon on a surface of a metal. The metal-enhanced fluorescence has advantages such as 1) improved fluorescence emission efficiency, 2) enhanced detection sensitivity, 3) prevention of photobleaching of fluorescent materials, and 4) applicability to all types of molecules including endogenous and exogenous chromophores, etc. In general, a metal suitable for metal-enhanced fluorescence includes metals having a high free electron density. Also, a continuous metallic thin film may exhibit enhance fluorescence emission when a fluorophore is disposed within 100 nm from a surface of the thin film.

Preferably, the nanoparticles of the first metal may be nanorods having an aspect ratio of 1.2 to 10. When the aspect ratio is less than 1.2, the core-shell nanocomposite may not exhibit a desired metal-enhanced fluorescence effect due to a decrease in scattering efficiency of the metal nanoparticles. On the other hand, when the aspect ratio is greater than 10, it may be difficult to control the formation of the shell of the second metal.

Preferably, each of the first metal and the second metal may be independently gold, silver, copper, palladium, or platinum, but the present invention is not limited thereto. Examples of the metals may include materials having a metal-enhanced fluorescence effect as well known in the related art. In addition, metals capable of exhibiting a metal-enhanced fluorescence effect may be used without limitation. Preferably, the first metal and the second metal may be metals having the same or similar lattice parameters. Specifically, the first metal and the second metal may be selected from metals having a lattice parameter ratio of 1:1.4 to 1.4:1. According to aspects of the present invention, a shell of the second metal is preferably uniformly introduced onto a core of the first metal to have a constant thickness so that a fluorophore is disposed to be spaced apart a predetermined distance from a surface of the second metal. Therefore, the first metal and the second metal having the same or similar lattice parameters may be selected so that a shell of the second metal can be introduced onto nanorods of the first metal in the same lattice form with a constant thickness. For example, the metal most widely used for research on metal-enhanced fluorescence in the related art is silver. Therefore, when silver is introduced to form a shell of the second metal so as to exhibit metal-enhanced fluorescence, gold is preferably used as a material for nanoparticles of the first metal. Because gold is a highly reactive metal, it is desirable to introduce a polynucleotide having a constant length, which has a fluorophore bound to one end thereof. Also, gold has an advantage in which a silver shell may be uniformly introduced because gold has lattice parameters similar to silver.

To dispose the fluorophore at a constant distance from the nanorods of the first metal, the polynucleotide may be used as the linker. Examples of the polynucleotide may include single- or double-stranded DNA or RNA. More preferably, the linker may be DNA. In theory, one polymer having a constant length may be used to achieve the purpose of disposing the fluorophore at a constant distance from the nanorods of the first metal. However, because the polymer is a mixture of separate polymer strands which have a constant mean molecular weight but different molecular weights, that is, different lengths, in effect, it is not easy to purely separate polymer strands having a constant length. Meanwhile, a polynucleotide having a constant length may be easily obtained by synthesizing a polynucleotide by adjusting the number of nucleotides constituting the polynucleotide. Also, the polynucleotide such as DNA and RNA may bind to another strand having complementary bonds to form a double strand. In this case, a more rigid backbone whose length is more easily controlled may be provided. Meanwhile, a polynucleotide composed of several to several tens of nucleotides may be present in the form of a somewhat rigid rod without bending even when present as a single strand. In particular, because DNA is stable even under general reaction conditions unlike RNA which is easily degraded and thus requires special reaction conditions (RNase-free conditions), DNA may be useful for introducing a fluorophore to have a constant distance according to an object of the present invention.

Preferably, the fluorophore spaced apart a constant distance from a surface of the shell of the second metal to be exposed to the outside may be embedded by further coating an external surface of the core-shell nanocomposite with a silica shell, thereby obtaining more stable fluorescence signals. Also, the silica shell may further include a fluorophore to exhibit an additional effect of enhancing the fluorescence signals.

Figure 6:
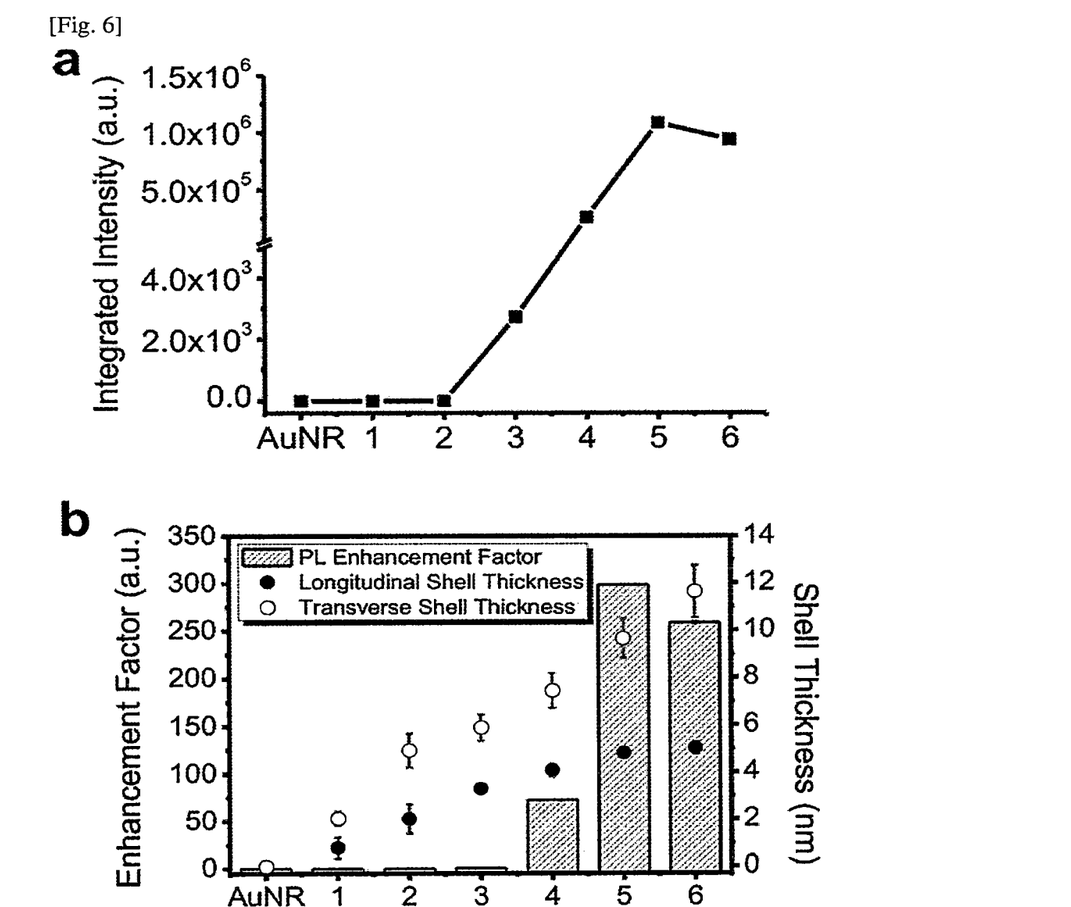
FIG. 6 includes graphs showing (a) integrated fluorescence intensities and (b) shell thicknesses and PL enhancement factors of the series of f-RNPs (f-RNP 1 to 6) according to one exemplary embodiment of the present invention.
Figure 7:
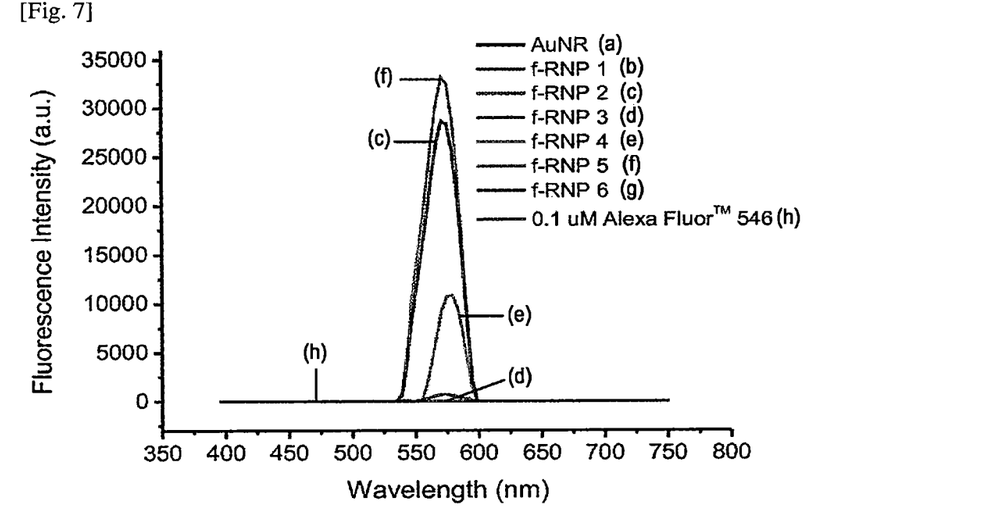
FIG. 7 is a graph showing fluorescence activities of the series of f-RNPs (f-RNP 1 to 6) and free Alexa Fluor™ 546 according to one exemplary embodiment of the present invention. The concentration of f-RNPs is 0.0728 nM. The highest fluorescence activity was observed for f-RNP 5.
Figure 8:
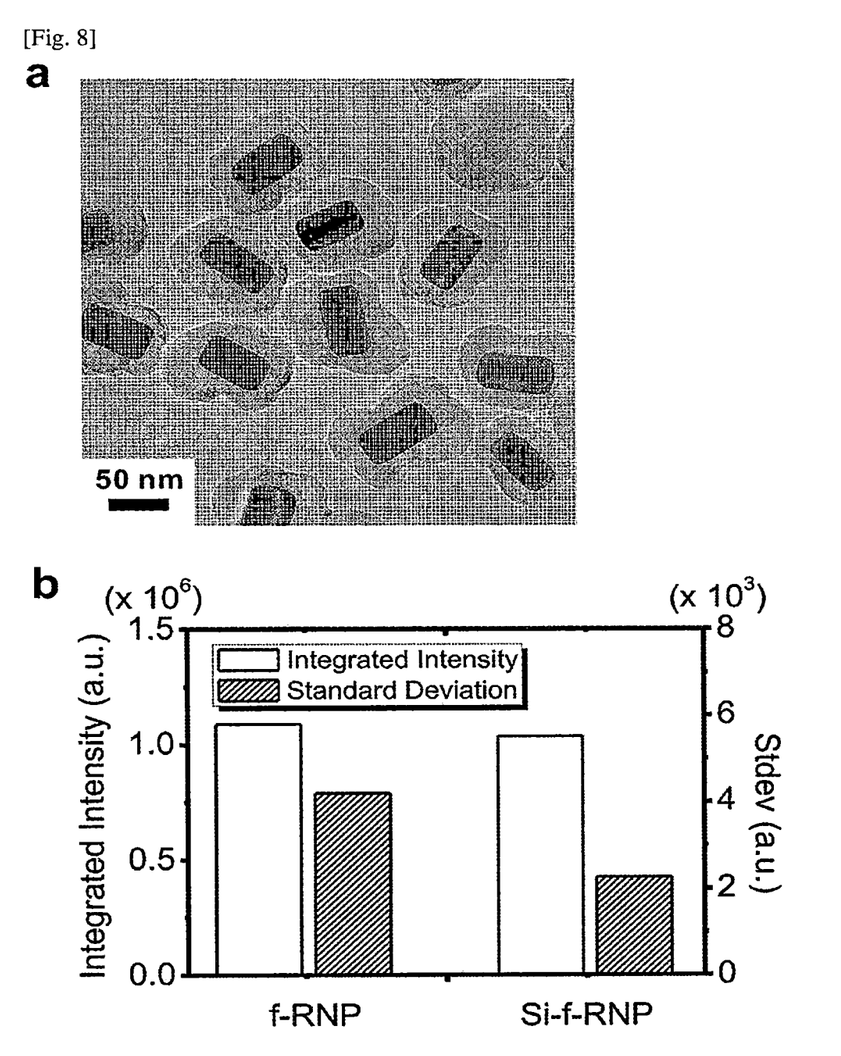
FIG. 8 is a diagram showing (a) a TEM image of silica-coated f-RNPs synthesized according to one exemplary embodiment of the present invention and (b) integrated fluorescence intensities of f-RNP 5 and silica-coated f-RNP 5 (Si-f-RNP 5).

According to one exemplary embodiment of the present invention, it can be seen that the core-shell nanocomposite into which a silver shell is introduced with a constant thickness after one end of thiolated DNA having a length of approximately 10 nm is labeled with Alexa Fluor 546 as a fluorophore and the other end is bound onto the gold nanorod may exhibit a metal-enhanced fluorescence effect when the fluorophore is disposed a predetermined distance from a surface of the shell (FIGS. 6 and 7). Also, it can be seen that the core-shell nanocomposite may have enhanced fluorescence signals having a more stable signal variation, that is, a smaller signal variation, by additionally introducing a silica shell onto the core-shell nanocomposite so that the exposed fluorophore is embedded in the silica shell to be fixed at the corresponding location (FIG. 8).

Further, the probe for metal-enhanced fluorescence including the core-shell nanocomposite according to the present invention is applicable to single-molecule detection due to excellent sensitivity, and thus may be effectively used as a biosensor for in vitro diagnosis of target diseases, intracellular tracking of biomaterials, in vivo imaging, solar cells, drug screening, gene sequencing, etc. when a target material or a detection material specifically binding to the target material is tagged with the probe.

MODE FOR INVENTION

Hereinafter, configurations and effects of the present invention will be described in further detail with reference to examples thereof. It should be understood that the following examples are merely provided to aid in understanding the present invention, but not intended to limit the scope of the present invention.

<Materials>

All chemical reagents ($HAuCl_4 \cdot 3H_2O$, CTAB, $NaBH_4$, L-ascorbic acid, $AgNO_3$, sodium-dodecyl sulfate (SDS), sodium chloride (NaCl), dithiothreitol (DTT), CTAC, EtOH, MeOH, 3-aminopropyltriethoxysilane (APTES), dimethylamine, and tetraethyl orthosilicate) were purchased from Sigma-Aldrich (St. Louis, Mo., USA), and used without additional purification. A HPLC-purified dye-coded thiolated oligonucleotide was purchased from IDT Inc. (Coralville, Iowa, USA), and reduced using dithiothreitol (0.1M)

dissolved in a phosphate buffer (170 mM, pH=8.0). Thereafter, the reduced oligonucleotide was purified though a desalting NAP-5 column (Sephadex G-25 medium, DNA grade). NANOpure H$_2$O (>18.0 MΩ) purified using a Milli-Q water purification system was used in all experiments. Alexa Fluor™ carboxylic acid, and succinimidyl ester fluorophores were purchased from Molecular Probes (Eugene, Oreg., USA). A HR-TEM (JEM ARM 200F, JEOL, Japan, 200 kV, FEI Company, Hillsboro, Oreg., USA) equipped with a formvar/carbon-coated copper grid (Ted Pella, Inc. Redding, Calif., USA) and an energy dispersive spectroscopy (EDS) unit (EDAX) were used for elemental mapping and lattice analysis, and other TEM images were obtained using JEM-2100 (JEOL, Japan, 200 kV). An inductively coupled plasma emission spectrometer (ICP-ES, ICPS-7510, Shimadzu, Japan) was used to measure a mass concentration of the prepared gold nanorods (AuNRs), and a NanoDrop 3300 fluorospectrometer was used to measure nanodrops. The shape of the formed gold nanorods was observed using a field-emission scanning electron microscope (FE-SEM, Helios 650, FEI, USA).

Example 1: Preparation of Gold Nanorods (AuNRs)

Figure 2:
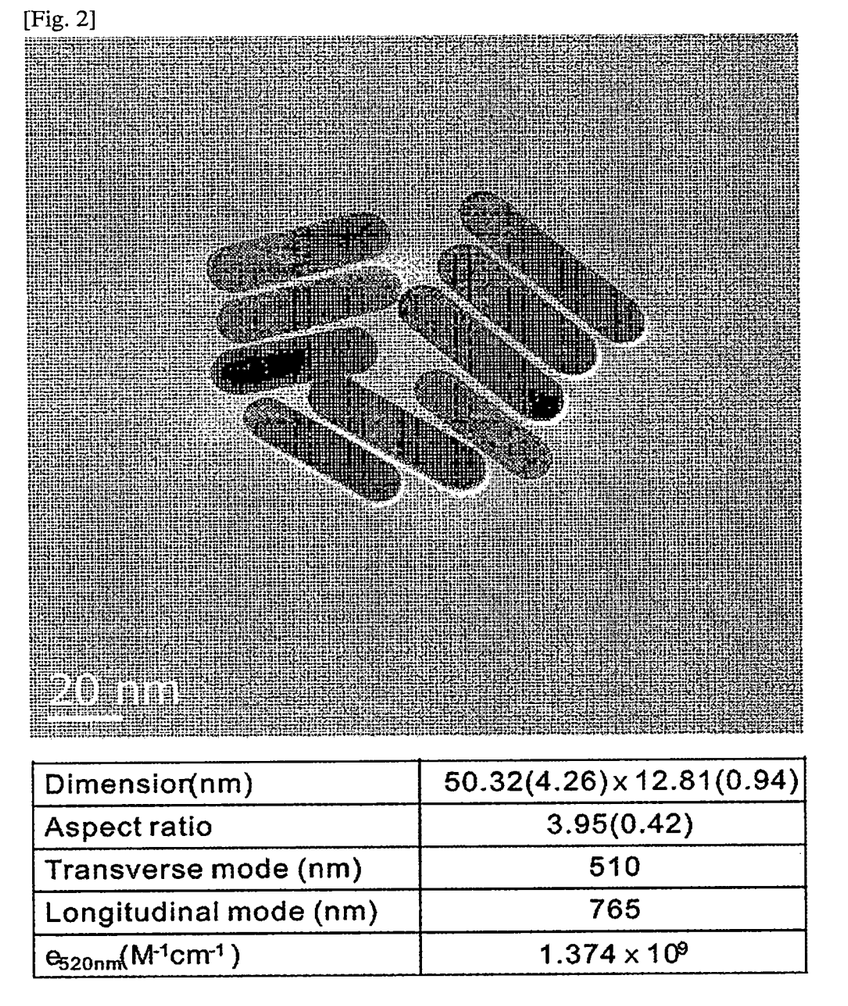
FIG. 2 is a diagram showing a TEM image of pre-synthesized AuNR and calculated physical and optical properties of the pre-synthesized AuNR. The pre-synthesized AuNR was analyzed using UV-visible spectrometry, TEM and ICP-AES to sufficiently measure dimensional and optical characteristics.

AuNRs having an aspect ratio value of approximately 4.0 were manufactured using a slightly modified seed-mediated method known in the art. Specifically, a seed was prepared by mixing 5 mL of a 0.5 mM HAuCl$_4$.3H$_2$O solution with 5 mL of 0.2 M CTAB, and 600 μL of an ice cold 0.01 M NaBH$_4$ solution was rapidly added thereto. The seed solution was used 2 hours after the reduction step. 5 mL of a 0.5 mM HAuCl$_4$.3H$_2$O solution was mixed with 5 mL of a 0.2 M CTAB solution, 200 μL of an AgNO$_3$ solution was added, and 70 μL of 78 mM L-ascorbic acid was then added thereto. After the resulting mixture was gently mixed, 12 μL of the seed solution prepared in advance was added, and the mixture was then incubated for at least 4 hours to obtain AuNRs. The AuNRs thus prepared were analyzed using TEM, UV-Vis spectrometry and an ICP-AES assay. The sizes and aspect ratios of 202 AuNRs were analyzed using ImageJ software. The AuNRs had a size of 50.32 (±4.26) nm×12.81 (±0.94) nm and an aspect ratio value of 3.95 (±0.42). It was revealed that a molar extinction coefficient (c) calculated at 520 nm was $1.374 \times 10^9$, and the absorbance at 520 nm was 0.249 when analyzed using ICP-AES. From these results, it was confirmed that a gold concentration of the prepared AuNRs solution was 69.5 μM. Transverse and longitudinal modes were observed at 510 and 765 nm, respectively (FIG. 2).

Example 2: Preparation of Fluorescence-Labeled DNA-Modified AuNRs by Salting Process An Alexa Fluor™ 546-modified thiolated oligonucleotide (DNA) was bound to a surface of AuNRs synthesized in Example 1. First, 1,500 μL of a newly reduced Alexa Fluor™ 546-modified thiolated oligonucleotide solution and 67.8 μL of a 10% SDS solution were mixed with 4,500 μL of a 1.16 nM AuNR solution. The mixed solution was incubated at room temperature for 30 minutes. Thereafter, the solution was diluted with a 100 mM phosphate buffer to reach a final phosphate concentration of 10 mM (pH 7.4), and then incubated at room temperature for 30 minutes. Three aliquots of 2 M NaCl (10 mM PB, 0.1% SDS) were added to boiling water every 20 minutes to form a 0.3 M NaCl solution. An hour after the final addition, the formed colloidal solution was centrifuged twice (at 9,500 rpm for 10 min), and the precipitate was re-dispersed in deionized water. Prior to a shell growth step, an optical density (OD) of DNA-modified particles was measured by a UV-vis spectrophotometer at 520 nm to determine a concentration of the DNA-modified particles.

Example 3: Quantification of Modified Oligonucleotides Per Single AuNR

Figure 3:
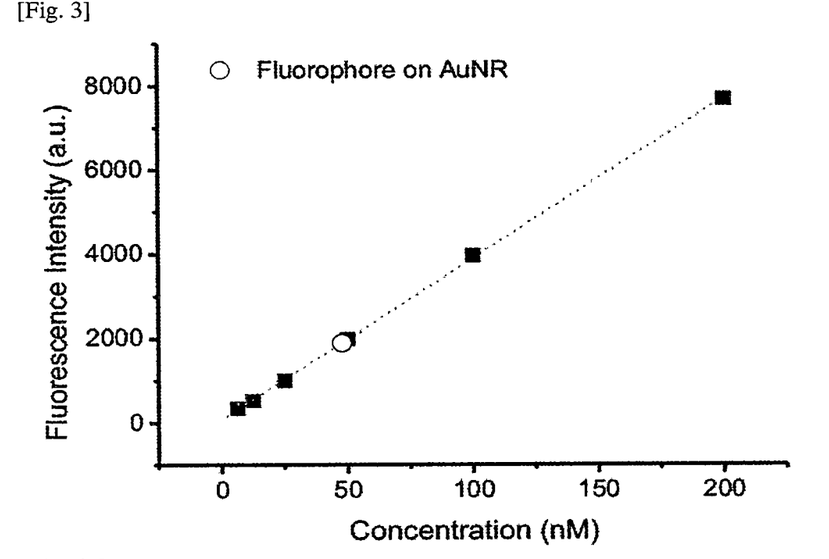
FIG. 3 is a graph showing quantitative analysis results of an Alexa Fluor™ 546-modified thiolated oligonucleotide on a surface of AuNR. On average, 293.4 Alexa Fluor™ 546-modified thiolated oligonucleotides are bound onto a surface of one AuNR.

To determine the number of dye-labeled oligonucleotides loaded on each AuNR particle, a concentration of AuNR nanoparticles and a concentration of fluorescent oligonucleotides in each sample were measured. To determine the concentration of an AuNR solution in each aliquot, a UV-visible spectrophotometer was used. The concentration of AuNR was directly associated with an absorbance value through Lambert-Beer's law (A=εbc). The molar extinction coefficient used in the present invention was $1.374$ $M^{-1}$ $cm^{-1}$ at 520 nm. To determine the concentration of the fluorescent oligonucleotides in each aliquot, 100 μL of the modified oligonucleotides in the AuNR solution was mixed with an equal volume of a 100 mM KCN solution to destroy an AuNR lattice structure, thereby separating the oligonucleotides from a surface of AuNR. In this step, the concentration of the oligonucleotides was diluted two-fold. The mixed solution was incubated to release the oligonucleotides into the solution and a supernatant was obtained to measure fluorescence intensity. The fluorescence intensity was compared to a free Alexa Fluor™ 546-modified thiolated oligonucleotide-based standard curve, and three different batches were measured to obtain a standard deviation (FIG. 3). For fluorescence measurement, the fluorophore was excited at 510 nm to measure fluorescence. As a result, it was confirmed that, on average, 293.4 fluorescent oligonucleotides were bound onto one AuNR particle.

Example 4: Formation of Silver Shell on Surfaces of Fluorescence-Labeled DNA-Modified AuNRs An Ag shell was formed on fluorescence-labeled DNA-modified AuNRs (DNA-AuNRs) and a thickness of the Ag shell was gradually increased. The AuNR solution prepared in Example 2 was diluted so that the OD at 520 nm became 0.5. A diluted AuNR solution (100 μL) was sequentially mixed with CTAC, AgNO$_3$ and a 0.1 M L-ascorbic acid solution, and the resulting mixture was incubated at 60° C. for 3 hours. The concentrations of the added reagents were sequentially 2.5 mM (f-RNP 1), 5.0 mM (f-RNP 2), 7.5 mM (f-RNP 3), 10.0 mM (f-RNP 4), 15.0 mM (f-RNP 5) and 20.0 mM (f-RNP 6) CTAC; and 0.25, 0.50, 0.75, 1.0, 1.5 and 2.0 mM AgNO$_3$, respectively. Specifically, the concentrations of CTAC and AgNO$_3$ increased while a molar ratio between CTAC and AgNO$_3$ was maintained at 10 to prepare a series of samples. After incubation, the resulting solutions were centrifuged at 7,000 rpm (f-RNP 1 and f-RNP 2), 6,000 rpm (f-RNP 3 and f-RNP 4) or 5,000 rpm (f-RNP 5 and f-RNP 6) for 10 minutes, and re-dispersed in deionized water. The manufactured fluorescence-labeled DNA-modified AuNRs having a shell formed on surfaces thereof were named fluorescent DNA-functionalized plasmonic rectangular nanoparallelepipeds, which were hereinafter abbreviated as f-RNPs. Each of the samples was distinguished by a number after the abbreviated name described above.

Example 5: Coating of f-RNPs with Fluorescent or Non-Fluorescent Silica Shell 3.5 μL of 0.2% 3-aminopropyltriethoxysilane (APTES) (v/v, an EtOH solution) was mixed with 62.5 μL of DMF and 8.4 µL of 0.8 mM carboxylic succinimidyl ester-tagged Alexa Fluor™ 546 (a MeOH solution). The resulting mixture was incubated at room temperature for 12 hours, and 700 µL of ethanol and 53.3 µL of a dimethylamine solution were added thereto. After 4 hours, 750 µL of the solution was mixed with 50 µL of 1.82 nM f-RNP 5 (a distilled water solution), and incubated for 30 minutes. Thereafter, 2 µL of 10% tetraethyl orthosilicate (v/v, an EtOH solution) was added thereto, and the resulting solution was incubated for another two and a half hours. The solution was centrifuged twice (at 5,000 rpm for 15 minutes), washed, and then re-dispersed in deionized water.

Example 6: Characterization of f-RNPs

The spectroscopic and morphological characteristics of f-RNPs were analyzed using a UV-visible spectrometer and TEM (FIG. 4). As an amount of a used Ag precursor increased, a remarkable spectroscopic change was observed. The f-RNPs 1 to 3 were compared with the AuNRs, and a wider transverse peak (at 510 nm) and a wider longitudinal peak (at 765 nm) were observed. As an amount of the used Ag precursor increased, the intensities of the two peaks also increased (FIG. 4C). From the TEM image (FIG. 4A), it was confirmed that the Ag shells had nearly identical thicknesses in both longitudinal and transverse directions in the case of the series of f-RNPs according to the present invention. It is known that the AuNRs having an aspect ratio of 3 to 7 have a [001] longitudinal growth direction; and an octagonal cross section enclosed by {100} and {110} facets, and {110} and {111} facets are exposed through a truncated region at an end side thereof. Initially, the thermodynamically induced conformal overgrowth occurred at the end and lateral regions of the AuNR. When an Ag growth step is proceeded using a CTAC capping agent, the {110} and {111} facets of the AuNR have a higher epitaxial growth rate than a {100} facet.

Figure 4A:
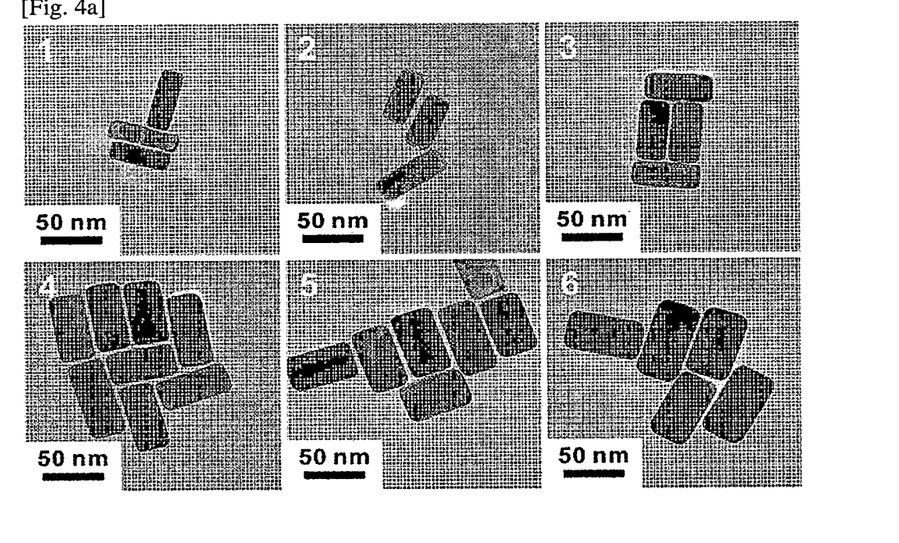
FIG. 4A is a diagram showing a TEM image of a series of f-RNPs (f-RNP 1 to 6) according to one exemplary embodiment of the present invention.
Figure 4B:
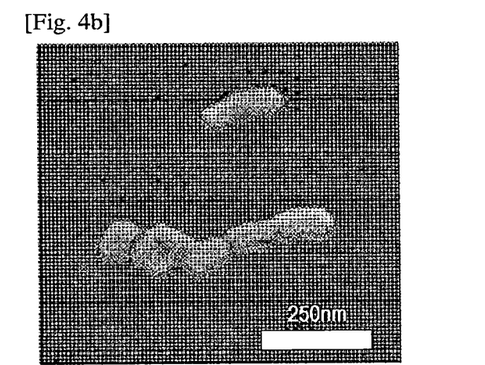
FIG. 4B is a diagram showing an SEM image of f-RNP 5 tilted at an angle of 52° according to one exemplary embodiment of the present invention.
Figure 4C:
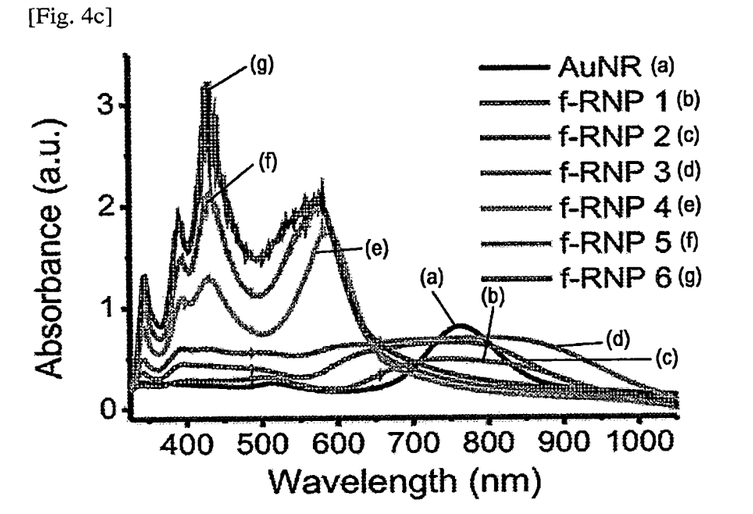
FIG. 4C is a graph showing UV-visible spectra of the series of f-RNPs (f-RNP 1 to 6) according to one exemplary embodiment of the present invention.

As the Ag shell grew, the Au—Ag core-shell particles were gradually surrounded by the {100} facet of Ag which is strongly bound to the capping agent, and the CTAC. For the f-RNPs 3 through 6, the Ag shells grew thicker in a transverse direction than in a longitudinal direction, and the f-RNPs had relatively sharp edges (FIG. 4A). Also, a rectangular parallelepiped 3-D shape of f-RNP 5 was determined using field-emission scanning electron microscopy measurement using a 52° tilt (FIG. 4B). From these results, it was confirmed that an end of the core-shell particle was more rapidly surrounded by the {100} facet, compared to the lateral regions. The CTAC strongly bound to a surface of Ag was able to block shell growth to induce a difference in shell growth rate between transverse and longitudinal directions of the core-shell particles after the f-RNP 3. Four distinct plasmonic modes were observed at 280 nm, 390 nm, 440 nm and 580 nm in the UV-visible spectrum (FIG. 4C). In particular, the plasmonic modes at 280 and 390 nm represent two distinct Ag shell formations (in longitudinal and transverse directions), and the plasmonic modes at 440 and 580 nm may account for transverse and longitudinal modes of the f-RNPs.

Figure 4D:
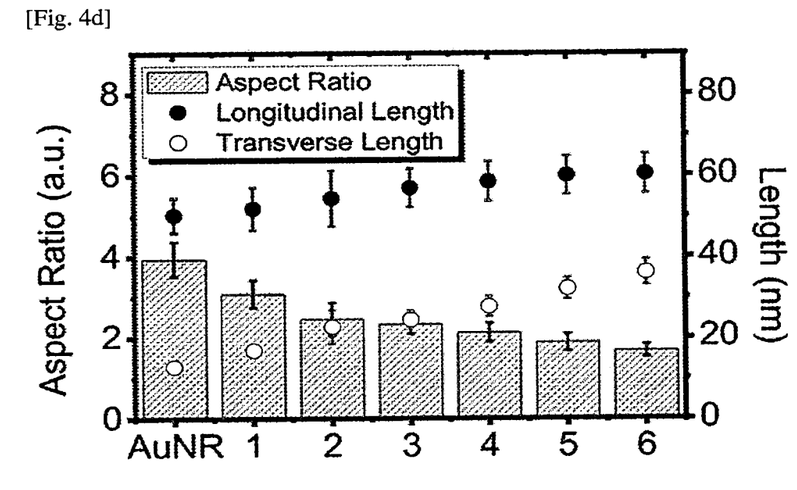
FIG. 4D is a diagram showing TEM-based statistical dimensional analysis results of the series of f-RNPs (f-RNP 1 to 6) according to one exemplary embodiment of the present invention.

Also, specific TEM analysis was performed using ImageJ software (rsb.info.nih.gov/ij/; FIG. 4D). For each of the f-RNP structures, at least 100 particles were measured. The transverse and longitudinal lengths of f-RNPs increased from 12.8 nm to 36.1 nm and from 50.3 nm to 60.4 nm, respectively, indicating that the thickness of the Ag shell is generally increased in a transverse direction. Mean transverse and longitudinal shell thicknesses were calculated by subtracting an AuNR dimension from the measured dimension of each of the f-RNPs. The transverse and longitudinal shell thicknesses were 11.6 and 5.0 nm, respectively. The transverse shell thickness (11.6 nm) of f-RNP 6 was similar to a theoretical length of the Alexa Fluor™ 546-modified thiolated oligonucleotide, whereas the longitudinal length of f-RNP 6 was much shorter than a theoretical length of the fluorescent oligonucleotide. The aspect ratios of the f-RNPs gradually decreased as the thickness of the formed Ag shell increased (FIG. 4D).

Figure 5:
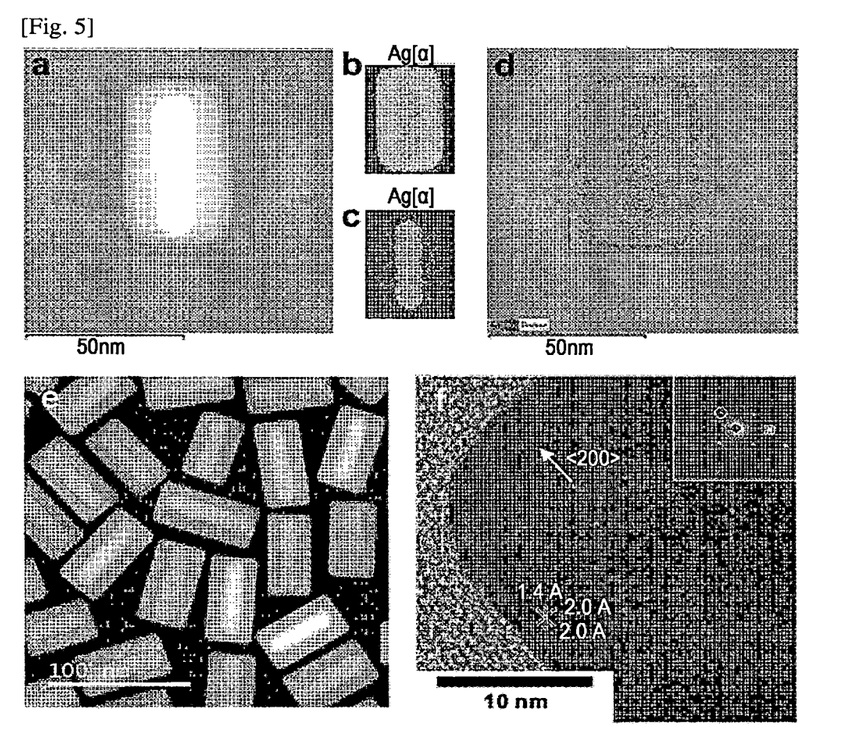
FIG. 5 is a diagram showing (a through d) elemental mapping images, (e) a dark-field TEM image, and (f) a HR-TEM and selected area electron diffraction (insert) image of f-RNP 5 according to one exemplary embodiment of the present invention.

To further analyze the structural characteristics of the f-RNPs, an elemental mapping image and lattice information of f-RNP 5 were obtained (FIG. 5). The results generally showed that the AuNR core and the Ag shell were clearly separated without intermixing between Au and Ag elements. The rectangular parallelepiped structures having well-defined sharp Ag corners were additionally confirmed on the dark-field TEM image (FIG. 5E). FIG. 5F shows a high-resolution TEM (HR-TEM) image and selected area electron diffraction (SAED) results. Clear and continuous fringes having a [001] lattice zone axis with a distance of 2.0 Å and capable of being indexed with {200} of face-centered cubic (fcc) Ag were observed on the HR-TEM image. The corresponding SAED patterns indicated square symmetry spots. From these results, it was confirmed that the Ag shell had a single crystal structure surrounded by the {100} facet. It can be seen that clear edges were observed in Ag shell corner regions on the HR-TEM image showing rectangular sections merged by the {100} facet.

Next, fluorescence signal enhancement for 2 µL of an f-RNP solution was measured using a NanoDrop 3300 fluorospectrometer (FIGS. 6 and 7). An integrated fluorescence intensity plot showed that the intensity of the fluorescence signal increased linearly as the Ag shell grew, from f-RNPs 3 through 5. For the f-RNP 6 having a transverse Ag shell having a thickness of approximately 12 nm, the fluorescence signals started to decrease when a fluorophore dye and the Ag shell were close to or in contact with each other. This indicates that the Ag shell is preferably formed in a state in which the fluorophore dye and the Ag shell were maintained at a proper distance apart, considering that a main difference between RNP 5 and RNP 6 arose from the transverse Ag shell thickness. Photoluminescence (PL) enhancement factors of the f-RNPs were calculated from the measured fluorescence intensities. The fluorescence signals of the f-RNPs were compared with the fluorescence signal of the free Alexa Fluor™ 546-modified thiolated oligonucleotide to obtain a PL enhancement factor for each of the f-RNP structures (FIG. 6B). The PL enhancement factor is defined as follows:

$$\frac{I_{MEF}/C_{MEF}}{I_{PL}/C_{PL}}$$

wherein $I_{MEF}$ and $C_{MEF}$ represent an integrated PL intensity of f-RNPs and a concentration of Alexa Fluor™ 546 in a solution. $I_{PL}$ and $C_{PL}$ represent an integrated PL intensity and a concentration of a free Alexa Fluor™ 546-modified thiolated oligonucleotide. Based on the results, it was confirmed that f-RNP 5 having transverse and longitudinal Ag shell thicknesses of 9.64 nm and 4.81 nm on a gold nanorod bound to DNA having a length of approximately 15 bp and a fluorophore labeled at one end, is a nanoprobe suitable for MEF, and the MEF enhancement factor for the f-RNP 5 probe in the solution was approximately 300.

Figure 1:
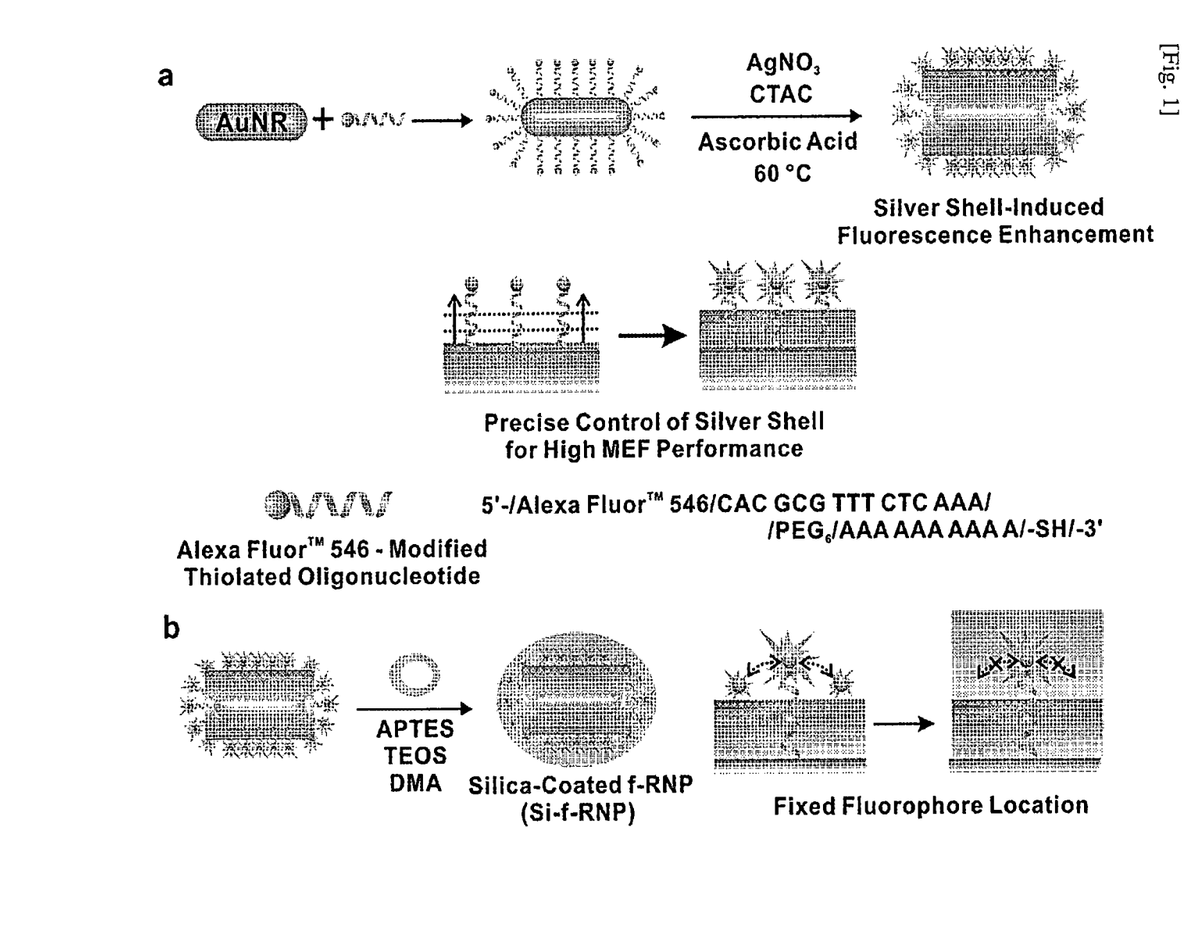
FIG. 1 is a diagram schematically showing a metal-enhanced fluorescence mechanism and a method of synthesizing (a) fluorescence-labeled DNA-modified-Au—Ag core-shell rectangular nanoparallelepipeds (f-RNPs) for a metal-enhanced fluorescence (MEF) application according to the present invention and (b) RNPs (Si-RNPs) whose surfaces are further coated with silica.

In addition, it was confirmed that the particle stability and biological toxicity of the f-RNPs were able to be improved when the particles were coated with the silica shell. In general, an Ag surface exposed to phosphate-buffered saline (PBS) or human serum is able to cause particle instability. Also, a deviation of the measured fluorescence signals increased when a distance between the fluorophore dye and the surface of the metal is fixed or variable due to the movement of the dye. After searching for optimal thickness of the Ag shell for MEF, a silica shell was formed so that the fluorophore was fixed at an optimized fluorophore location of f-RNPs, and the fluorophore was embedded in the silica shell to minimize a fluorescence signal fluctuation in a single particle and a fluorescence signal fluctuation from particle to particle (FIG. 1B).

Figure 9:
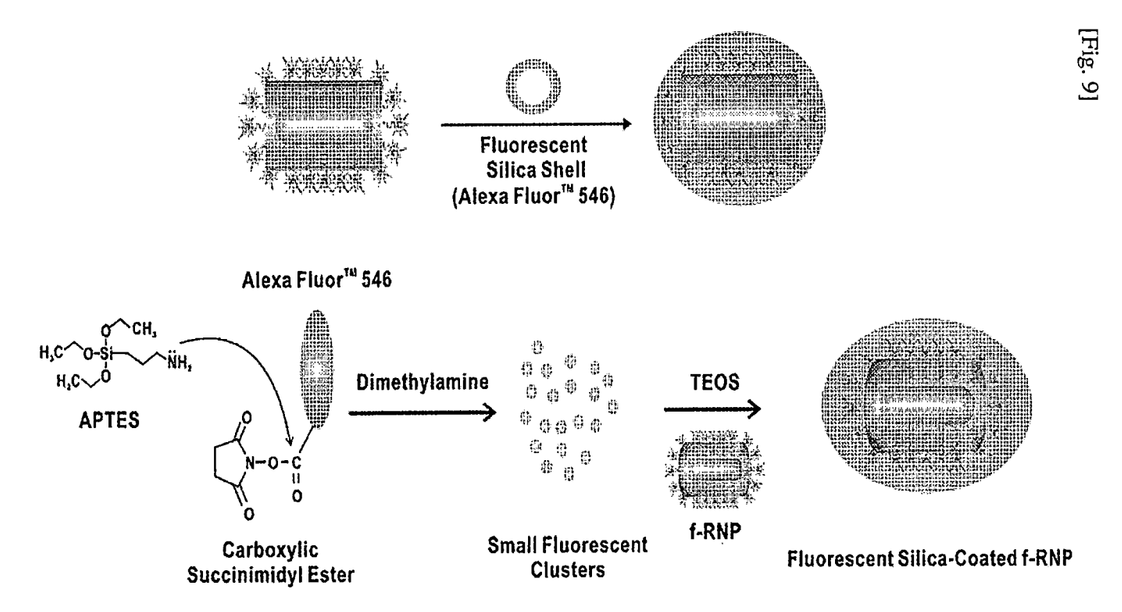
FIG. 9 is a diagram schematically showing a process of coating a surface of f-RNP with silica according to one exemplary embodiment of the present invention. A fluorescent silica shell is designed so that each of the f-RNPs exhibits higher fluorophore loading capacity as well as a fixed fluorophore location and improved stability.
Figure 10:
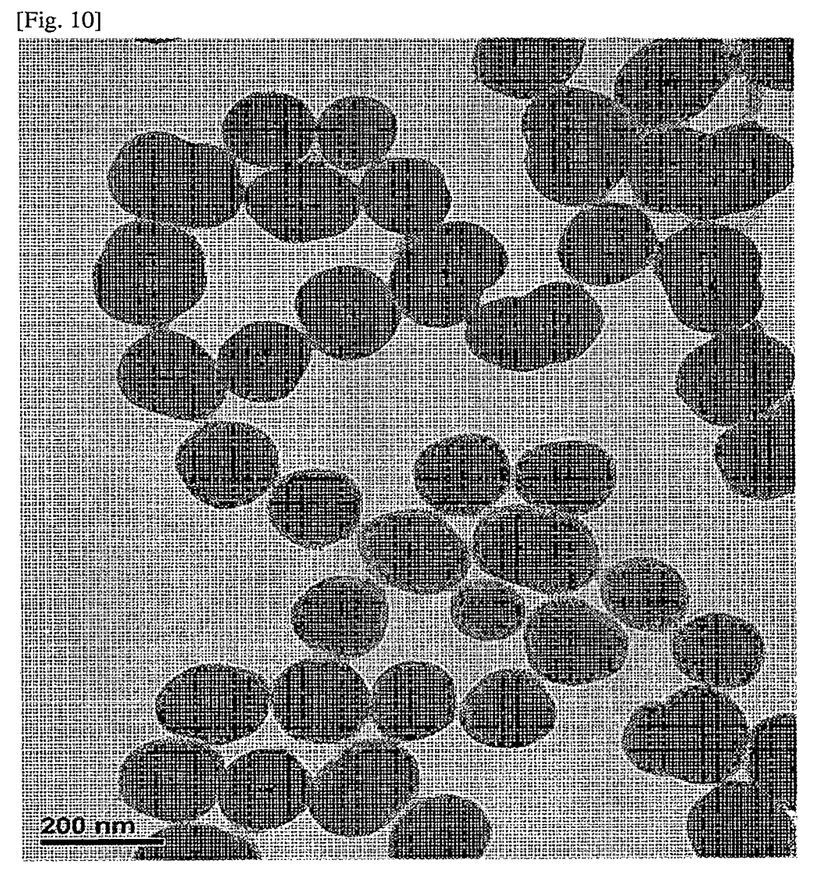
FIG. 10 is a diagram showing a TEM image of fluorescent silica-coated f-RNPs prepared according to one exemplary embodiment of the present invention. A silica-coated nanorod had a total size of approximately 150 nm, and the shape and size of a nanobar was maintained during a silica coating process.

In a representative experiment for forming the silica shell, 3.5 μL of 0.2% (v/v, in EtOH) APTES was mixed with 762.5 μL of EtOH and 53.3 μL of a dimethylamine solution. After the resulting solution was kept at room temperature for 4 hours, 750 μL of the solution was mixed with 50 μL of a 1.82 nM f-RNP 5 solution dissolved in distilled water, and the mixed solution was additionally incubated at room temperature for 30 minutes. Thereafter, 2 μL of 10% (v/v, in EtOH) tetraethyl orthosilicate was added thereto, and the resulting solution was incubated at room temperature for 2.5 hours. The solution was centrifuged twice (at 5,000 rpm for 15 minutes), and then re-dispersed in deionized water. A TEM image was measured to determine whether a silica shell was formed on f-RNPs (FIG. 8A). As a result, the f-RNPs were completely enclosed by the silica shell, and almost all the silica shells included the f-RNPs. Next, differences in fluorescence signal intensity and reproducibility activity between f-RNP 5 and silica-coated f-RNP 5 (Si-f-RNP 5) were determined. As a result, the fluorescence signal intensities were very similar before and after silica coating. However, a standard deviation of the fluorescence signal intensity of Si-f-RNP 5 decreased compared to the f-RNP 5, indicating that the signal reproducibility was able to be further improved through silica shell formation (approximate 2-fold improvement in standard deviation; FIG. 8B). In this case, when additional fluorescent molecules were embedded in the silica shell for coating during a process of forming the silica shell, the fluorescence intensity of each of the particles was able to be further improved (FIGS. 9 and 10).

To summarize, the present inventors developed a synthetic strategy for screening an optimal RNP probe for MEF by using fluorescence-labeled DNA whose length was adjustable and adjusting a thickness of a silver shell formed by precisely regulating the shell-forming chemistry to adjust a distance between a labeled fluorophore and a surface of the silver shell on the DNA. For this purpose, the structural and optical characteristics of f-RNPs were specifically analyzed. It was revealed that a PL enhancement factor of approximately 300 for the solution samples was realized under the optimized conditions. In addition, the present inventors confirmed that the stability and signal reproducibility of the probe was improved through formation of the silica shell on the f-RNPs. The Si-f-RNP structure may be a promising platform for practical use of the MEF probe. The present inventors expect that the strategies and results according to the present invention provide benefits for use of the MEF probe in better understanding of the MEF probe, reliable quantitative research using the MEF probe, chemical and biological detection, and bio-imaging applications.

The invention claimed is:

1. A fluorescent monomeric core-shell nanocomposite material comprising:
    a nanoparticle of a first metal;
    a plurality of linkers each having a uniform length bound to said first metal via one end thereof and having a fluorophore bound to the other end thereof, and
    a shell of a second metal directly formed on said nanoparticle to which said linkers are bound,
    wherein the shell comprises a thickness such that a surface of the shell is spaced apart a uniform distance from each of said fluorophores in a vertical direction,
    wherein said plurality of fluorophores are coated with a silica shell, and
    wherein said silica shell comprises a silica shell fluorophore that extends from said silica shell.

2. The core-shell nanocomposite material of claim 1, wherein said nanoparticle of said first metal comprises a nanorod having an aspect ratio of 1.2 to 10.

3. The core-shell nanocomposite material of claim 1, wherein said first metal and said second metal are independently selected from the group consisting of gold, silver, copper, palladium and platinum.

4. The core-shell nanocomposite material of claim 1, wherein said first metal and said second metal have a lattice parameter ratio of 1:1.4 to 1.4:1.

5. The core-shell nanocomposite material of claim 1, wherein said linkers are a single- or a double-stranded polynucleotide.

6. A probe for metal-enhanced fluorescence comprising a core-shell nanocomposite material of claim 1.

7. The core-shell nanocomposite material of claim 1, wherein said fluorophores on said plurality of linkers are identical.

8. The core-shell nanocomposite material of claim 1, wherein said silica shell fluorophore and said plurality of fluorophores on said linkers are identical.

9. The core-shell nanocomposite material of claim 1, wherein said nanocomposite material exhibits a metal-enhanced fluorescence effect.

10. A method of manufacturing a core-shell nanocomposite material comprising a plurality of fluorophores each disposed to have a uniform distance from a surface thereof in a vertical direction, said method comprising:
    binding one end of each of a plurality of linkers having a uniform length onto a nanoparticle of a first metal, wherein the other end of said linker has a fluorophore bound thereof;
    forming a shell of a second metal directly on said nanoparticle of said first metal to which the linkers are bound by adjusting a thickness of the shell of the second metal such that a surface of the shell of the second metal is [to be] spaced apart a uniform distance from the fluorophore; and
    coating said core-shell nanocomposite material with a silica shell, wherein said silica shell comprises a silica shell fluorophore that extends from said silica shell.

11. The method of claim 10, wherein said nanoparticle of said first metal comprises a nanorod having an aspect ratio of 1.2 to 10.

12. The method of claim 10, wherein each of said first metal and said second metal is independently selected from the group consisting of gold, silver, copper, palladium and platinum.

13. The method of claim 10, wherein said first metal and said second metal have a lattice parameter ratio of 1:1.4 to 1.4:1.

14. The method of claim 10, wherein said linkers are a single- or a double-stranded polynucleotide.

15. The method of claim 10, wherein said fluorophores on said plurality of linkers are identical.

16. The method of claim 10, wherein said silica shell fluorophore and said plurality of fluorophores on said linkers are identical.

* * * * *